(12) United States Patent
Wehinger et al.

(10) Patent No.: US 11,173,293 B2
(45) Date of Patent: Nov. 16, 2021

(54) HAND-HOLDABLE TATTOO DEVICE

(71) Applicant: TCA Systems GmbH, Vienna (AT)

(72) Inventors: Georg Wehinger, Vienna (AT); Roland Maria Reininger, Dornbirn (AT); Maroua Meherzi, Vienna (AT)

(73) Assignee: TCA SYSTEMS GMBH, Vienna (AT)

( * ) Notice: Subject to any disclaimer, the term of this patent is extended or adjusted under 35 U.S.C. 154(b) by 230 days.

(21) Appl. No.: 16/326,981

(22) PCT Filed: Oct. 4, 2017

(86) PCT No.: PCT/EP2017/075126
§ 371 (c)(1),
(2) Date: May 1, 2019

(87) PCT Pub. No.: WO2018/069093
PCT Pub. Date: Apr. 19, 2018

(65) Prior Publication Data
US 2020/0016389 A1    Jan. 16, 2020

(30) Foreign Application Priority Data
Oct. 13, 2016  (AT) .................................. A 474/2016

(51) Int. Cl.
*A61M 37/00*  (2006.01)
(52) U.S. Cl.
CPC ..... *A61M 37/0076* (2013.01); *A61M 2205/11* (2013.01)

(58) Field of Classification Search
CPC .......... A61M 37/0076; A61M 37/0084; A01K 11/00; A01K 11/005; A61B 2017/0023; A61B 2017/3435; A61B 2017/3441
See application file for complete search history.

(56) References Cited

U.S. PATENT DOCUMENTS 5,741,290 A * 4/1998 Hsieh ................ A61M 37/0076
606/185
6,345,553 B1 * 2/2002 Adler ..................... A45D 34/04
30/362
(Continued)

FOREIGN PATENT DOCUMENTS

DE    299 19 199    2/2000
DE    103 43 590    4/2005
(Continued)

OTHER PUBLICATIONS

International Search Report dated Dec. 14, 2017 in International (PCT) Application No. PCT/EP2017/075126.

*Primary Examiner* — Darwin P Erezo
*Assistant Examiner* — Brigid K Byrd
(74) *Attorney, Agent, or Firm* — Wenderoth, Lind & Ponack, L.L.P.

(57) ABSTRACT

A hand-holdable device for tattooing includes a handle part with a drive, a needle module which is detachably secured to the handle part and includes a needle that can be moved back and forth by the drive, and a protective sleeve which is configured to fully isolate the needle module from the handle part. The needle is connected to the drive by a form-fitting and/or magnetic coupling including coupling elements and the protective sleeve is releasably held between the coupling elements.

17 Claims, 4 Drawing Sheets

(56) References Cited

U.S. PATENT DOCUMENTS

| | | | |
|---|---|---|---|
| 6,689,095 B1* | 2/2004 | Garitano | A61M 37/0076 604/70 |
| 2002/0069726 A1* | 6/2002 | Adler | A45D 34/04 81/9.22 |
| 2004/0116953 A1* | 6/2004 | Dixon | A61M 37/0076 606/186 |
| 2006/0020283 A1* | 1/2006 | Lisec | A61M 37/0076 606/185 |
| 2010/0036317 A1* | 2/2010 | Oginski | A61M 37/00 604/131 |
| 2011/0048174 A1* | 3/2011 | Lin | A61M 37/0084 81/9.22 |
| 2012/0123462 A1* | 5/2012 | Lee | A61M 37/0076 606/185 |
| 2015/0025561 A1* | 1/2015 | La Fontaine | A61M 37/0076 606/186 |
| 2015/0151098 A1 | 6/2015 | Spendlove et al. | |
| 2016/0184572 A1* | 6/2016 | Xiao | A61M 37/0076 606/186 |

FOREIGN PATENT DOCUMENTS

| | | |
|---|---|---|
| DE | 203 21 463 | 8/2007 |
| DE | 10 2011 120 366 | 6/2013 |
| EP | 1 618 915 | 1/2006 |
| WO | 2015/003578 | 1/2015 |
| WO | 2015/084475 | 6/2015 |

* cited by examiner

HAND-HOLDABLE TATTOO DEVICE

BACKGROUND OF THE INVENTION

1. Field of the Invention

The invention relates to a hand-held device for tapping into the skin with a handle piece comprising a drive, a needle module detachably secured on the handle piece that comprises a needle movable back and forth by means of the drive, and a protective sleeve that fully isolates the needle module from the handle piece.

The hand-held device according to the invention serves in particular for tattooing, creating permanent make-up and for medical and cosmetic applications of any type.

2. Description of the Related Art

Observing hygiene regulations in the case of hand-held devices of this type is a particular challenge since the needle pierces the surface of the skin and the device consequently comes into contact notably with blood or body fluids.

Prior art discloses (for example in U.S. Pat. No. 6,505,530 B2) the use of a hand-held device with a detachably secured needle module, in which a needle module is detachably secured on a handle piece, whereby the part of the hand-held device, specifically the needle module, that comes into direct contact with the skin to be treated, can be disposed of after use. It is furthermore disclosed in this prior art to utilize diaphragms in order to establish an isolation between two segments in the interior of the hand-held device. However, the problem in particular of the exterior contamination of the handle with body fluids, such as blood, and ink is not resolved thereby.

WO 2015/003578 A1, in turn, discloses the use of a protective sleeve which extends between the needle module and the handle or over the handle. While this protective sleeve solves the problem of possible contamination of the handle, however, based on its complicated structure, the protective sleeve is subject to damage due to its disposition between the needle module and the handle as well as due to the force transmission from the drive to the needle, wherein WO 2015/003578 A1 does not contain any precise and practical disclosure regarding the manner in which a reliable connection between needle module and handle, or the drive and the needle, can be established without incurring damage to the protective sleeve.

SUMMARY OF THE INVENTION

The invention therefore addresses the problem of providing a device of the above described class with which the simple and safe disposition of the protective sleeve between the needle module and the handle can be accomplished.

This problem is resolved in a device of the class described in the introduction thereby that the needle is connected to the drive by means of a form-closure and/or magnetic coupling with coupling elements and that the protective sleeve is releasably retained between the coupling elements.

In the case of the invention the magnetic coupling is especially preferred. Specifically, if the protective sleeve is secured between the coupling elements of the magnetic coupling, it can be structured very simply without there existing the risk of damage.

This applies in particular if the needle module, due to a needle change in the course of creating a tattoo, has to be changed rather frequently since through the magnetic securement of the protective sleeve between the coupling elements the risk of damage is non-existent.

As is known per se, the needle module comprises a front end with an aperture for the needle and a back end via which the needle module is releasably connected with the handle piece. The handle piece furthermore preferably comprises an extension or a recess via which the location of the back end of the needle module is fixed in position on the handle piece.

In the case of the invention it is further preferred if the end, facing the needle module, of the drive-side coupling elements is substantially aligned with the front end of the extension. It can thereby be achieved that the protective sleeve at the transition between needle module and handle is substantially disposed straight or planar whereby a very simple structure of the protective sleeve can be obtained with a substantially cylindrical center part and a substantially straight or planar, front-face forepart.

Further preferred embodiments of the invention are subject matter of the additional dependent claims.

BRIEF DESCRIPTION OF THE DRAWINGS

Further features and advantages of the invention are evident based on the following description of a preferred embodiment example of the invention with reference to the attached drawing. Therein depict.

DETAILED DESCRIPTION OF THE INVENTION

Figure 1:
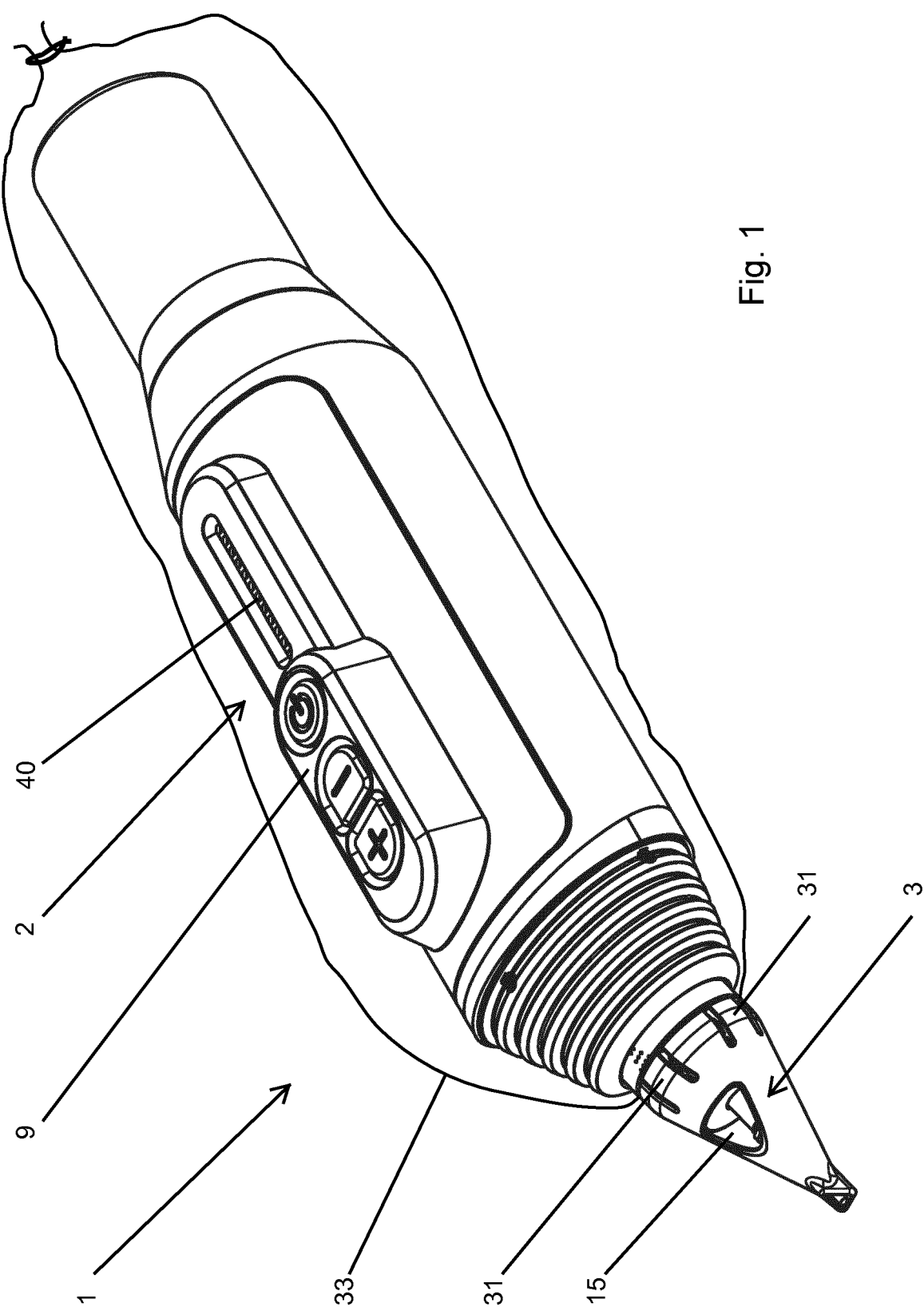
FIG. 1 a perspective view of a hand-held device according to the invention.
Figure 2:
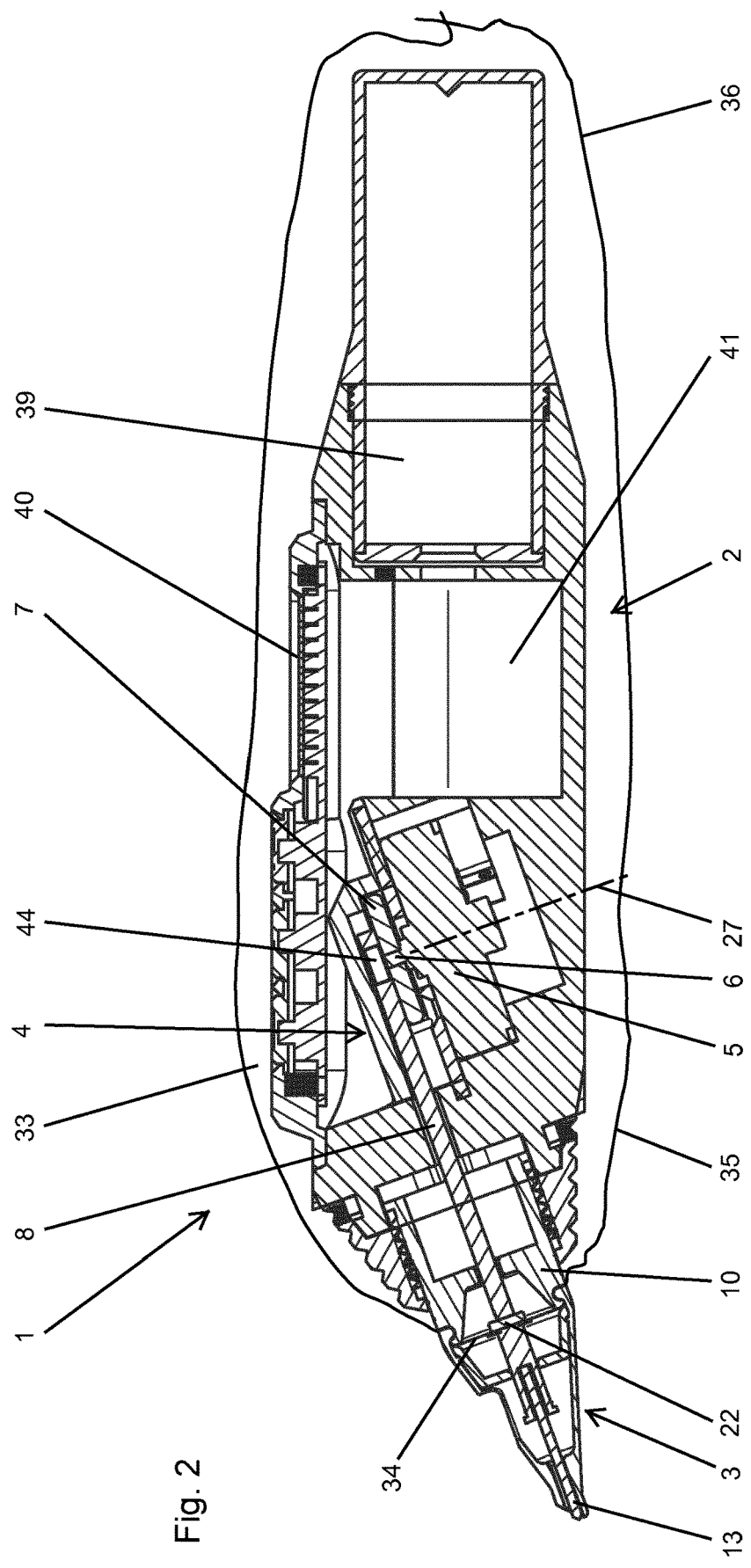
FIG. 2 a longitudinal section through the hand-held device of FIG. 1.
Figure 3:
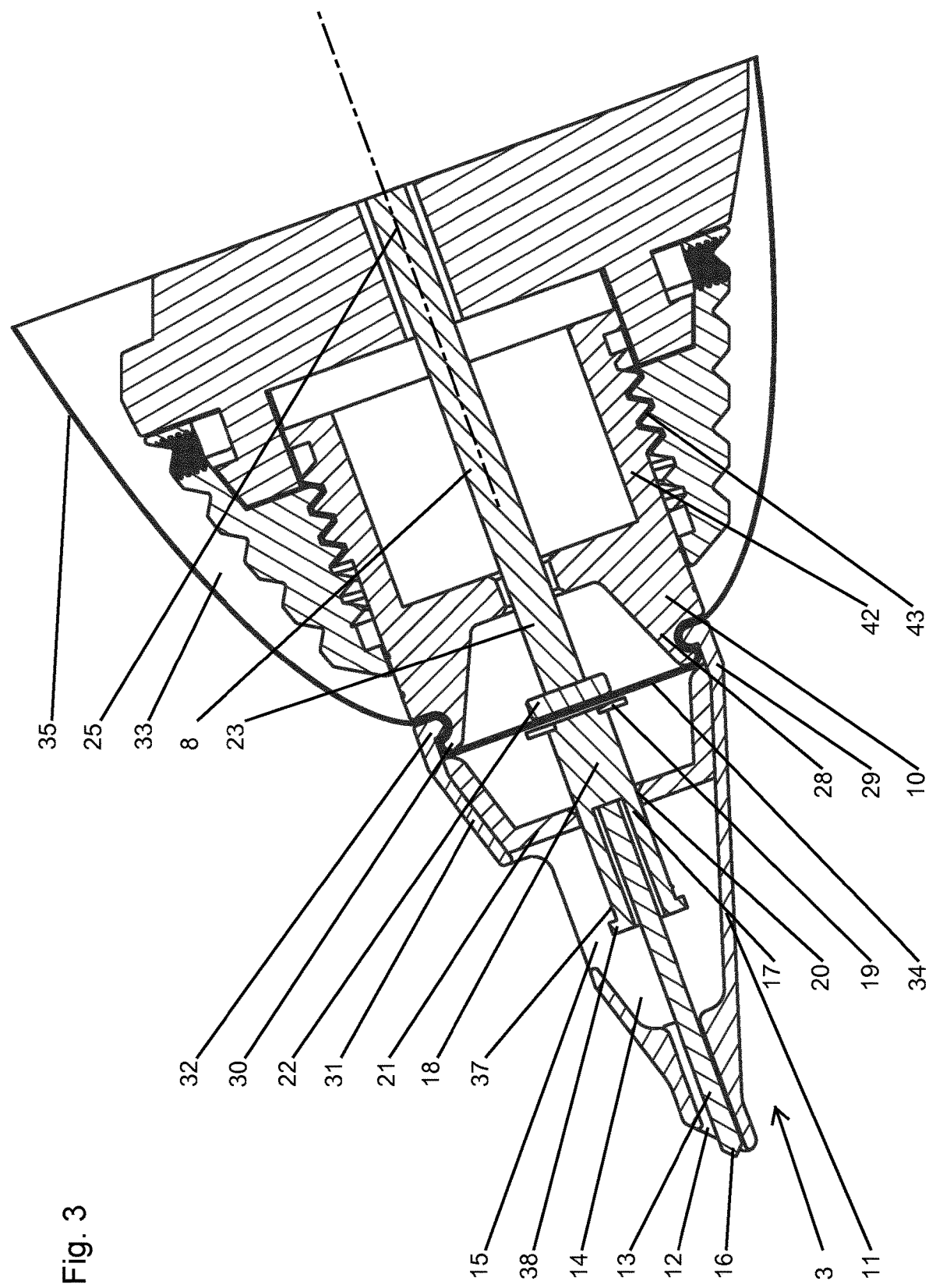
FIG. 3 a section through the front end of the hand-held device at a larger scale, and FIG. 4 a top view onto a segment of the hand-held device in the proximity of the drive.
Figure 4:
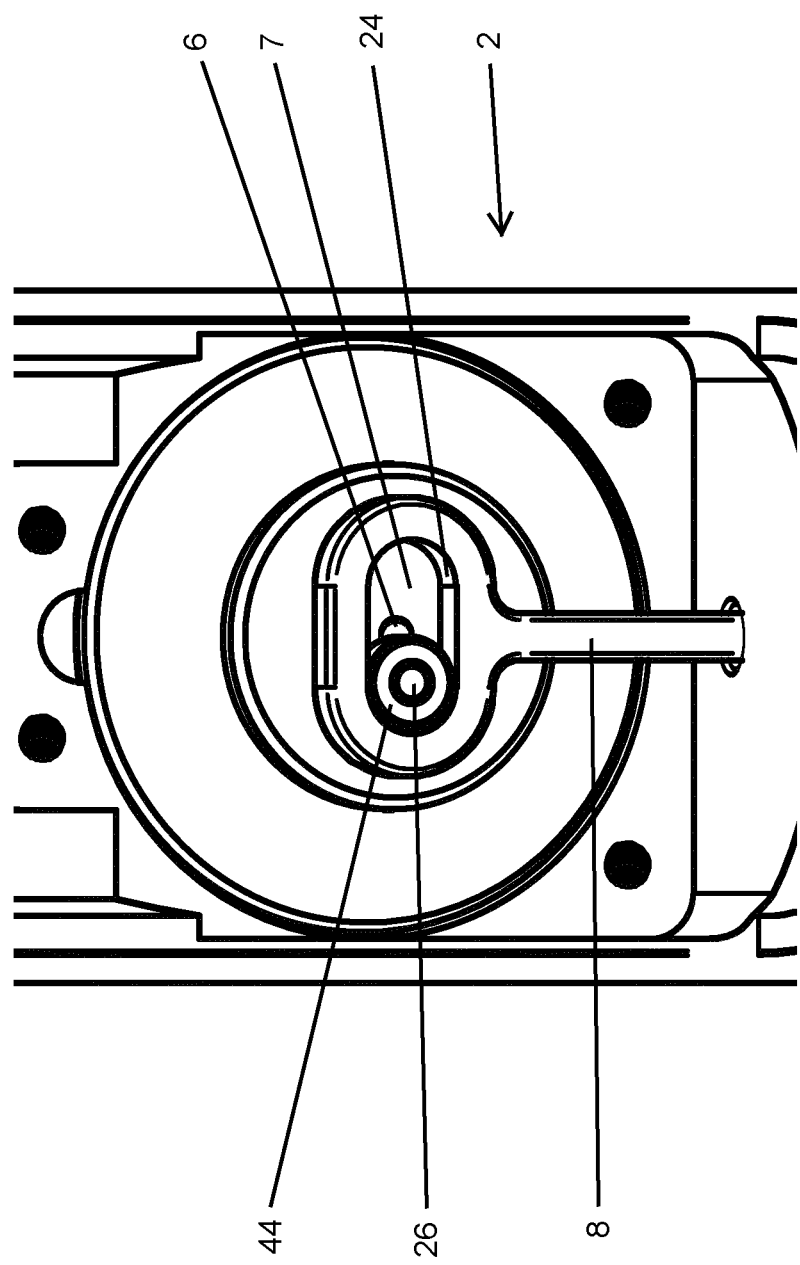

The Figures show a preferred embodiment of a hand-held device 1 according to the invention that comprises a handle piece 2 and a needle module 3 releasably secured thereto. In the handle piece 2 is disposed a drive 4 which comprises a—symbolically depicted—electric motor 5, a driving disk 7 disposed on a shaft 6 of the electric motor 5 and a driving rod 8. On the handle piece 2 there are furthermore disposed operating elements 9 for switching-on and switching-off and for the control of the speed or frequency of a needle 13. The handle piece 2 comprises additionally a receptacle 39 for a battery or an accumulator for the power supply of the drive motor 5 and of a, not shown, control of the hand-held device 1, a display 40 of the battery charge and of the frequency of the needle 13 and a receiving volume 41 for the control of the hand-held device 1.

At the front end 10 of handle piece 2 is releasably secured the needle module 3 which is substantially comprised of a housing 11 with an aperture 12 for the needle 13 and a receiving volume 14 with a filling aperture 15 for ink. The filling aperture 15 can also be utilized for cleaning the needle module 3. The needle 13 which, within the scope of the invention, can have any desired or conventional form with one or several tips 16, is preferably connected at its end, located oppositely the tip 16, with a retainer 17. The needle 13 comprises at its back end, thus at the end facing the handle piece 2, a first coupling element 19. The retainer 17 is displaceably supported in an aperture 20 of a guide plate 21, wherein the guide plate 21 also delimits the receiving volume 14 toward the handle piece 2.

Associated with the first coupling element 19 is a second coupling element 22 which is disposed at the front end 23 of the driving rod 8. In the preferred embodiment of the invention at least one of the two coupling elements 19, 22 is magnetic, with the other coupling element 19, 22 being either also magnetic or at least magnetizable. In the case of the invention it is preferred for the coupling element 22 on the driving rod 8 to be magnetic and the coupling element 19 on the retainer 17 of the needle 13 to be magnetizable and to be comprised for example of a small plate or a ring of iron.

Through the magnetic coupling, comprised of the two coupling elements 19 and 22, the back and forth motion of the driving rod 8 is directly transmitted to the retainer 17 and subsequently onto the needle 13.

Alternatively or additionally, in the case of the invention a connection under form closure is also feasible thereby that, for example, one coupling element is implemented as a ball and the other coupling element as a corresponding socket into which the ball is snapped-in.

On the side opposite to the second coupling element 22 an elongated hole 24 is disposed on the driving rod 8, whose longitudinal axis is oriented transversely to a longitudinal axis 25 of the driving rod 8. In the elongated hole 24 is received a drive journal 26 which, where appropriate, can also comprise a roller 44 supported thereon in order to effect greater running smoothness or lesser wear. The drive journal 26 is disposed spaced apart at a certain radius from the rotational axis 27 of the electric motor 5 on the driving disk 7, wherein the elongated hole 24 has a length that is preferably minimally greater than the twofold radius (plus the diameter of the drive journal 26 or the roller 44) and a width that corresponds approximately to the diameter of the drive journal 26 or the roller 44. The driving disk 7 is rotated through the rotation of motor 5 whereby the drive journal 26 is moved back and forth in the elongated hole 24 and simultaneously the driving rod 8, and therewith also the needle 13, is moved translationally or in a straight line back and forth in the direction of the longitudinal axis 25.

The longitudinal axis 25 of the driving rod 8 and consequently also the rotational axis 27 of motor 5 are inclined with respect to a longitudinal axis or main axis of the handle piece 2, whereby an ergonomic grip or holding is enabled for the operating personnel while handling the hand-held device 1 according to the invention.

The handle piece 2 comprises at its front end 10 an extension 28 via which the position of the back end 29 of the needle module 3 is fixed. In the depicted preferred embodiment the needle module 3 lies from the outside in contact on the sleeve-shaped or annularly implemented extension 28. However, the extension 28 can also have a different form and can be, for example, spherical or polygonal, in particular octagonal. It would also fundamentally be feasible for the back end 29 of the needle module 3 to be inserted into the extension 28 or into the recess formed therein.

In the preferred embodiment on extension 28 a protrusion 30 is disposed, projecting outwardly and in particular having the form of an annular flange, and at the back end 29 of housing 11 of the needle module 3 latching fingers 31 are disposed with detents of protrusion 32 which engage behind the protrusion 30 and in this manner fix the housing 11 of the needle module 3 on the handle piece 2. It is understood that instead of a snap-on connection between the needle module 3 and the handle piece 2, other connection means can also be utilized, for example a magnetic connection with one or several magnets at the front end 10 in the proximity of extension 28 and one or several magnets or magnetizable elements on housing 11 of needle module 3.

For the protection of handle piece 2, in particular against blood and ink, a protective sleeve 33 is provided which is only shown schematically in the drawing. The protective sleeve 33 extends at least in the proximity of the front end 10 facing the needle module 3 over the handle piece 2 and isolates the handle piece 2 completely from the needle module 3.

The protective sleeve 33 comprises a front segment 34 and a center segment 35 adjoining thereon, with the front segment 34 extending between the handle piece 2 and the needle module 3 and the center segment 35 adjoining thereon extending over the front end of the handle piece 2. The protective sleeve 33 comprises preferably, but not mandatorily, also additionally a back segment 36 that extends up to and over the back end of the handle piece 2 and is here closed, whereby the handle piece 2 is completely and gaplessly enclosed by the protective sleeve 33.

The center segment 35 and the optionally available back segment 36 of the protective sleeve 33 can be implemented such that they are closely or loosely in contact on the handle piece 2.

The back end of the protective sleeve 33 can be closed, for example by means of an adhesive strip, a clamp or by knotting the protective sleeve 33.

The magnetic coupling, comprised of the two coupling elements 19 and 22, is preferably disposed such that the end, facing the needle module 3, of the drive-side coupling element 22 is substantially aligned with the front end or the front face of extension 28. This means that the end, facing the needle module 3, of the drive-side coupling element 22 and the front end or the front face of extension 28 are substantially within the same plane. The front segment 34 is in this manner substantially oriented straight or planar and the region adjoining thereon of the protective sleeve 33 is fixed in the connection region between the needle module 3 and the handle piece 2, whereby, due to the relatively short connection region, a simple assembly and disassembly of the needle module 3 on the handle piece 2 is ensured with a very low risk of damage to the protective sleeve 33.

However, it is fundamentally also feasible for the front segment 34 not to be oriented straight or at right angles to the longitudinal axis 25 of the driving rod 8, but rather minimally obliquely and thus be oriented, for example, substantially in the form of a cone in the direction toward the handle piece 2 or toward the needle module 3.

The contact faces of the coupling elements 19 and 22 are preferably planar or nearly planar and, if appropriate, have additionally minimally rounded-off edges whereby high punctiform stress of the protective sleeve 33 which could damage the protective sleeve 33 can be avoided.

During the back and forth motion of the driving rod 8 the front segment 34 of the protective sleeve 33 is only moved back and forth in the dimensional extent of the excursion of the driving rod 8, for example approximately 4 mm, such that the protective sleeve 33 is only exposed to very low stress in this region, whereby the mechanical stress can also be kept very low through the magnetic retention of the protective sleeve 33 between the coupling elements 19 and 22.

In order to prevent the risk of injuries through the needle 13 during the emplacement and removal of the needle module 3 onto or from the handle piece 2, a snap-latching mechanism is provided. Herein on the retainer 17 a preferably annular projection 37 is disposed which has a spacing from a flange 38, disposed at the front end of the retainer 17, which corresponds approximately to the wall thickness of the guide plate 21 and has an outer diameter that is minimally greater than the diameter of aperture 20 in the guide plate 21. When the needle module 3 is detached from the handle piece 2, the retainer 17 is initially still retained back through the magnetic coupling 19, 22 whereby the retainer 17 with the needle 13 is retracted until the tip 16 of needle 13 is located behind the aperture 12 and thus no longer represents an injury risk. The projection 37 is herein pressed through the aperture 20 and comes to be located at the side of the guide plate 21 facing the handle piece 2, with the flange 38 being in contact on the opposite side of the guide wall 21. The edge of the aperture 20 consequently forms a press-fit mating surface for the projection 37. The retainer 17 with the needle 13 is consequently fixed in a safe position. The magnetic connection of the coupling elements 19, 22 is subsequently released and the needle module 3 is completely detached.

When plugging the needle module 3 onto the extension 28 of the handle piece 2, the retainer 17, after the magnetic coupling 19, 22 has been completed, is pressed forwardly whereby the projection 37 is again pressed through aperture 20 and the tip 16 of needle 13 is pushed outwardly through aperture 12.

The dimensional extent by which the needle 13 or its tip 16 projects from aperture 12 can according to the invention be set or adjusted by means of a setting ring or annulus 42 that forms the front end 10 with extension 28. The setting ring 42 is screwed in via a threading 43 into the handle piece 2 such that by rotating the setting ring 42 (with the needle module 3 removed) its position can be varied in the direction of axis 25 with respect to the driving rod 8 or the needle 13, whereby the dimensional extent by which the needle 13 or its tip 16 projects from the aperture 12 can be varied.

The invention claimed is:

1. A hand-holdable device for tapping into skin, the hand-holdable device comprising:
   a handle piece including a drive;
   a needle module releasably secured on the handle piece with a needle that can be moved back and forth by the drive; and
   a protective sleeve which is configured to fully isolate the needle module from the handle piece,
   wherein:
   the needle is connected with the drive by form-closure and/or magnetic coupling with coupling elements;
   the protective sleeve is releasably retained between the coupling elements;
   the needle module includes a front end with an aperture for the needle and a back end via which the needle module is releasably connected with the handle piece;
   the handle piece includes an extension via which a position of the back end of the needle module is fixed in position on the handle piece;
   one of the coupling elements is on a drive-side;
   an end of the one of the coupling elements faces the needle module and is configured to align with a front end of the extension; and
   the protective sleeve extends at least partially over the handle piece.

2. The hand-holdable device of claim 1, wherein the needle module is connected with the handle piece across a snap-on connection at or adjacent to the extension.

3. The hand-holdable device of claim 1, wherein the needle module is connected with the handle piece across a magnet connection at or adjacent to the extension.

4. The hand-holdable device of claim 1, wherein the needle module is in contact with the extension.

5. The hand-holdable device of claim 4, wherein:
   an outwardly projecting protrusion is disposed on the extension; and
   the outwardly projecting protrusion is configured to engage at least one latching finger on the back end of the needle module.

6. The hand-holdable device of claim 5, wherein the outwardly projecting protrusion is an annular flange.

7. The hand-holdable device of claim 1, wherein the protective sleeve extends up to a back end of the handle piece and is closed such that the protective sleeve is configured to gaplessly enclose the handle piece.

8. The hand-holdable device of claim 1, wherein:
   the one of the coupling elements is a first of the coupling elements;
   the needle is disposed on a first end of a retainer;
   a second of the coupling elements is disposed on a second end of the retainer; and
   the first end of retainer is opposite to the second end of the retainer in a longitudinal direction of the retainer.

9. The hand-holdable device of claim 8, wherein:
   a snap-on element is disposed on the retainer; and
   in a retracted position of the needle, the snap-on element is releasably retained on a mating surface of the needle module.

10. The hand-holdable device of claim 9, wherein the snap-on element is a projection.

11. The hand-holdable device of claim 1, wherein:
    the drive includes a driving rod that is oriented coaxially with the needle and configured to move translationally; and
    the one of the coupling elements is disposed on the driving rod.

12. The hand-holdable device of claim 11, wherein a rotational axis of a drive motor of the drive is oriented at a right angle with respect to a longitudinal axis of the driving rod.

13. The hand-holdable device of claim 11, wherein:
    the driving rod includes an elongated hole oriented transversely to a longitudinal axis of the driving rod;
    the elongated hole is disposed at an end of the driving rod opposite to the one of the coupling elements; and
    the elongated hole is configured to receive a drive journal connected with a motor shaft.

14. The hand-holdable device of claim 13, wherein the elongated hole is configured to receive the drive journal with a roller supported on the drive journal.

15. The hand-holdable device of claim 1, wherein the hand-holdable device is configured to be battery operated or accumulator operated.

16. The hand-holdable device of claim 1, wherein the extension is disposed on a setting ring that is mounted on the handle piece so as to be adjustable in a longitudinal direction of the needle.

17. The hand-holdable device of claim 16, wherein the setting ring is mounted on the handle piece via a threading.

* * * * *